United States Patent [19]

Bressner

[11] Patent Number: 5,681,063
[45] Date of Patent: Oct. 28, 1997

[54] CONNECTOR ASSEMBLY FOR DOUBLE TUBING

[75] Inventor: Gorm Bressner, Providence, R.I.

[73] Assignee: E.R. Squibb & Sons, Inc., Princeton, N.J.

[21] Appl. No.: 563,847

[22] Filed: Nov. 28, 1995

[51] Int. Cl.$^6$ .................................................. F16L 39/00
[52] U.S. Cl. ................ 285/360; 285/376; 285/133.1; 285/138
[58] Field of Search .................................. 285/360, 376, 285/377, 133.1, 138

[56] References Cited

U.S. PATENT DOCUMENTS

| | | | |
|---|---|---|---|
| 448,261 | 3/1891 | Ridge | 285/133.1 |
| 917,204 | 4/1909 | Walther | 285/360 |
| 1,221,935 | 4/1917 | White | 285/376 |
| 1,525,794 | 2/1925 | Blake | 285/360 |
| 1,541,139 | 6/1925 | Hayden et al. | 285/377 |
| 1,947,593 | 2/1934 | Hamilton | 285/360 |
| 2,221,284 | 11/1940 | Folsom | 285/376 |
| 2,317,729 | 4/1943 | Bruno | 285/377 |
| 2,823,699 | 2/1958 | Willis | 285/376 |
| 3,129,993 | 4/1964 | Ross | 285/360 |
| 5,005,875 | 4/1991 | Harte | 28/360 |

FOREIGN PATENT DOCUMENTS 367363  3/1963  Switzerland ............. 285/360

Primary Examiner—Eric K. Nicholson
Attorney, Agent, or Firm—Stuart E. Krieger

[57] ABSTRACT

The connector assembly for double tubing includes a pair of interengageable coupling members that engage when latches on the respective coupling members are aligned in a predetermined nonlatching position. Locking of the coupling members together is accomplished by rotating one of the coupling members with respect to the other coupling member to interengage the respective latches of each coupling member. A latch section of one of the coupling members extends transversely of the coupling member body and a latch section of the other coupling member extends longitudinally of the coupling member body. A locking notch in one of the latch sections receives the other latch section to place the coupling members in a locked position when one of the coupling members is rotated to engage the latches. Further rotation of the coupling members unlatches the respective latch members to permit separation of the coupling members upon imposition of oppositely directed forces on each of the coupling members. Whether the coupling members are engaged in a locked or unlocked condition, fluid flow through the coupling members is maintained because engagement of the coupling members aligns the fluid flow tubes of each coupling member in leak-tight fashion.

23 Claims, 4 Drawing Sheets

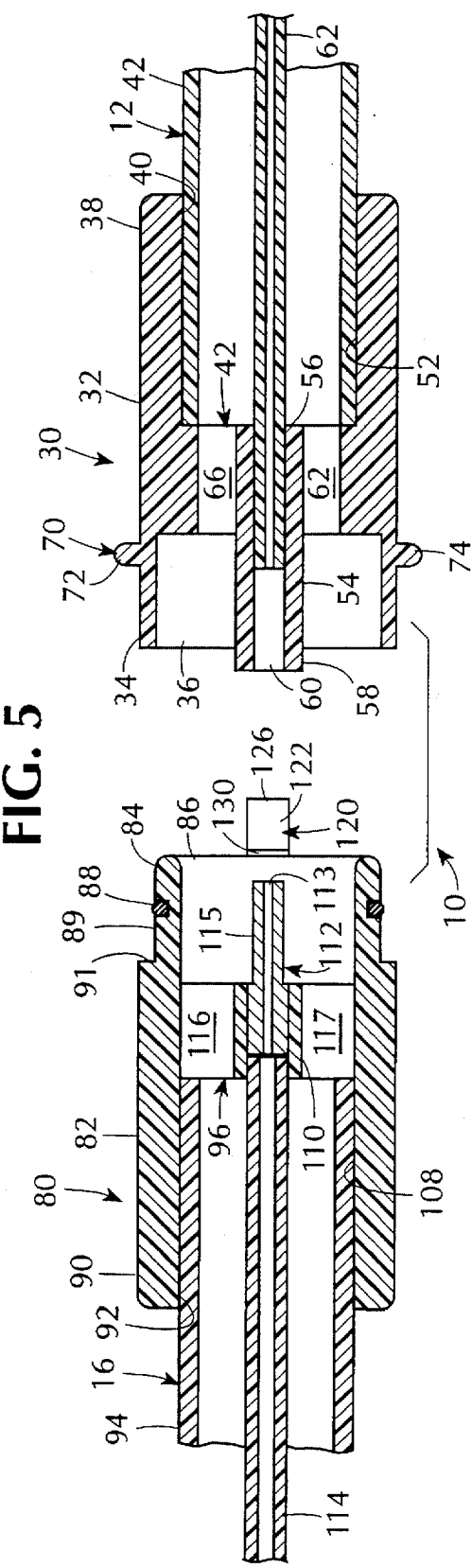
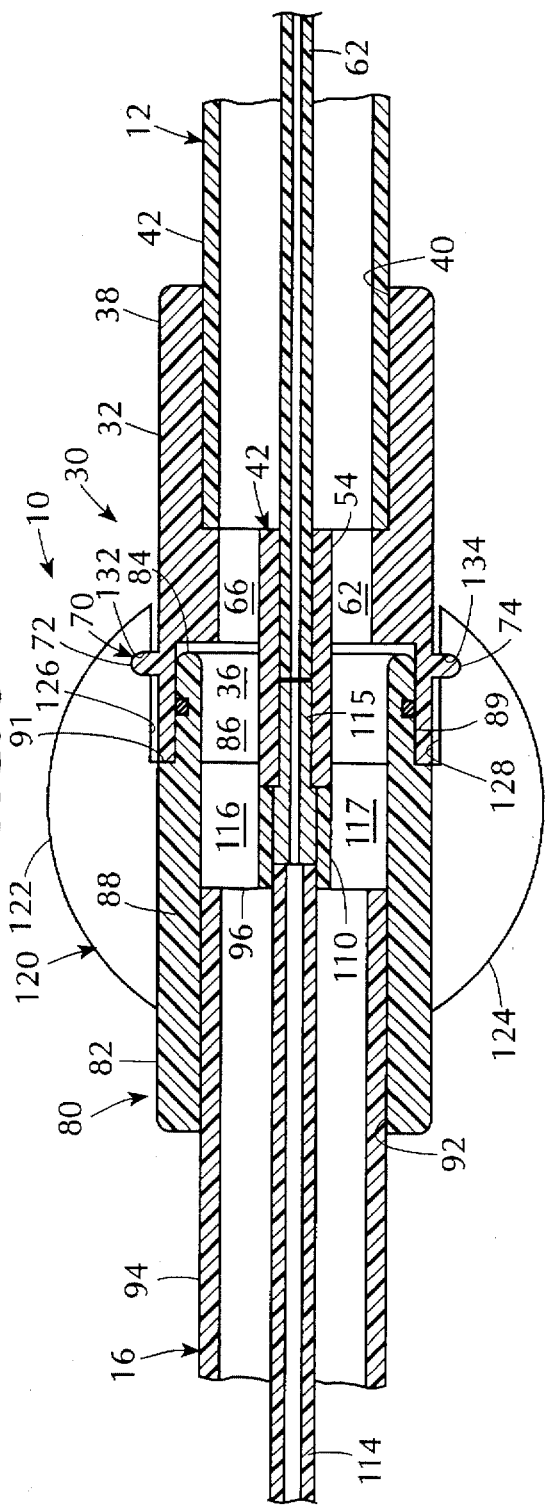
FIG. 5
FIG. 6

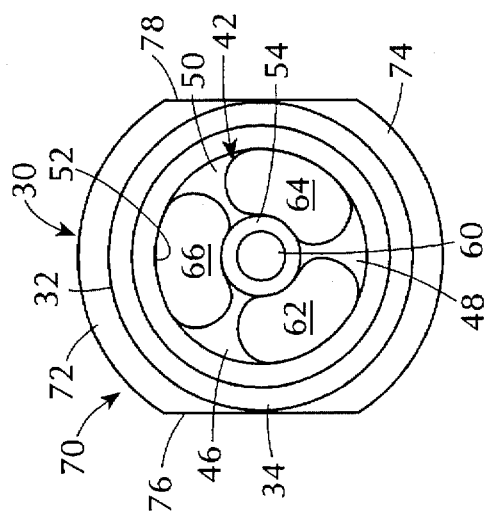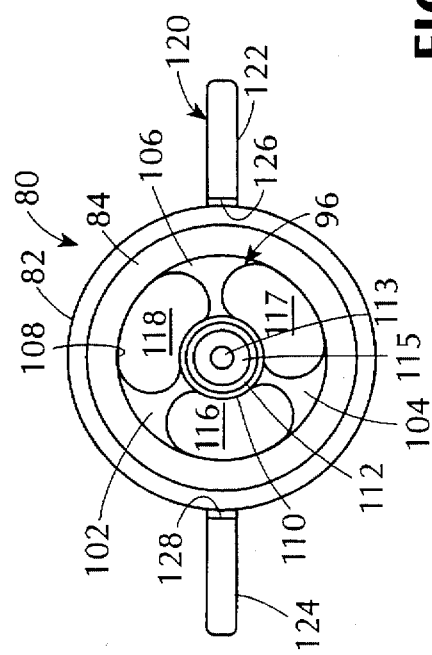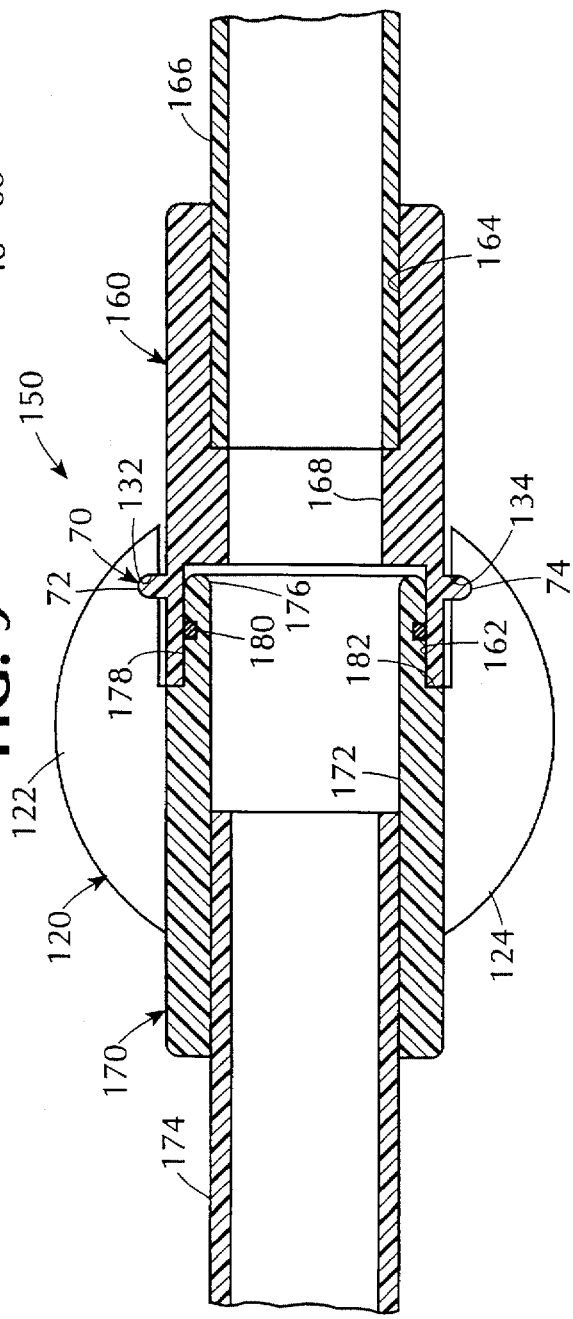

CONNECTOR ASSEMBLY FOR DOUBLE TUBING

BACKGROUND OF THE INVENTION

This invention relates to connector assemblies for tubing and more particularly to a novel connector assembly for double tubing that can be easily engaged and locked together, and easily unlocked and disengaged.

Double tubing constructions usually include concentrically spaced inner and outer tubes or pipes such as shown in U.S. Pat. No. 724,310. The end of one of the disclosed double pipe sections is telescoped into the end of another double pipe section to connect the double pipe sections. Since the connected sections are held together by telescoping engagement, such pipe sections are separable by pulling one section away from the other section.

In instances where a relatively strong connection is desired between double pipe sections a welded joint is used as shown in U.S. Pat. No. 1,481,255. However, welded sections are not easily separable and must often be broken away if removal is desired.

Threaded engagement between double tubing or double pipe sections provides removable securement as shown in U.S. Pat. Nos. 2,838,074 and 5,088,774, among others. Threading is arduous and time consuming and is also impractical for elongated or flexible double tubing which can become twisted or tangled during threading and unthreading.

While quick release coupling assemblies are generally known for connecting single tube sections together, they are usually not adaptable to double tubing sections because of potential interference between the coupling mechanism and the inner tube of a double tube assembly.

It is thus desirable to provide a connector assembly for double tubing that permits easy engagement, locking and release of double tube sections without interfering with the inner tube of a double tube structure.

OBJECTS AND SUMMARY OF THE INVENTION

Among the several objects of the invention may be noted the provision of a novel connector assembly for double tubing, a novel connector assembly for double tubing that is free of moving parts, a novel connector assembly for double tubing that can be formed in a molding operation, a novel connector assembly for double tubing that can be axially rotated into either a locked or unlocked condition, a novel connector assembly for double tubing that does not interfere with the inner tube of a double tube, a novel connector assembly for double tubing that is lightweight, easy to construct and simply to operate, and a novel method of providing releasable connection between sections of double tubing.

Other objects and features of the invention will be in part apparent and in part pointed out hereinafter.

In accordance with the present invention, the connector assembly for double tubing includes a pair of coupling members adapted to engage together in a leak-tight fluid flow position, whether the coupling members are locked to each other or in a condition of separable engagement. Latches are provided on each of the coupling members to selectively lock the coupling members together in their engaged fluid flow position.

Preferably the latches include mating flange-like structures formed on the exterior surface of each of the coupling members. One of the latches includes a locking flange engageable in a locking recess of the other latch upon axial rotation of one of the engaged coupling members with respect to the other engaged coupling member. A latch release surface, provided on one of the latches, is alignable with the locking recess to place the latches in an unlocked condition.

When the coupling members are initially engaged in a leak-tight fluid flow position, the latches are in an unlocked condition. Axial rotation of one of the engaged coupling members relative to the other engaged coupling member through a predetermined angle places the latches in a locked condition. Such rotation does not upset the leak-tight relationship between the engaged coupling members.

The coupling members, upon axial rotation to a condition of unlocked engagement, are separable upon imposition of oppositely directed forces on each of the coupling members. When the coupling members are in a locked engagement, they cannot be separated by imposition of the oppositely directed forces on each coupling member, but must first be axially rotated through a predetermined angle to the unlocked position before separation can be accomplished.

In one embodiment of the invention, each of the coupling members include support means for supporting an inner tube within the confines of an outer tube. Engagement of the coupling members aligns the outer and inner tubes held by each coupling member such that fluid flow through the inner tube does not communicate with fluid flow through the outer tube.

In another embodiment of the invention, the inner tube support means are eliminated from the coupling members, and the coupling members are adapted to support a single tube.

Whether the coupling members are adapted to support double tubes or single tubes, the latch structure for each connector system can be identical.

The connector assembly for double tubing is also adaptable to support more than one inner tube, since the latching arrangement for the connector assembly does not interfere with the inner tube fluid flow path.

The coupling members for the connector assembly can each be formed as a single piece and are thus easy to manufacture and suitable for use in disposable systems which employ double tubes or single tubes.

The invention accordingly comprises the constructions and method hereinafter described, the scope of the invention being indicated in the claims.

DESCRIPTION OF THE DRAWINGS

In the accompanying drawings,

FIG. 5 is a sectional view corresponding to FIG. 2;

FIG. 6 is a sectional view corresponding to FIG. 4;

FIG. 7 is an end view of the engagement end of the left-hand connector component of FIG. 2;

FIG. 8 is an end view of the engagement end of the right-hand connector component of FIG. 2; and FIG. 9 is a sectional view of another embodiment of the invention.

Corresponding reference characters indicate corresponding parts throughout the several views of the drawings.

DETAILED DESCRIPTION OF THE INVENTION

Figure 1:
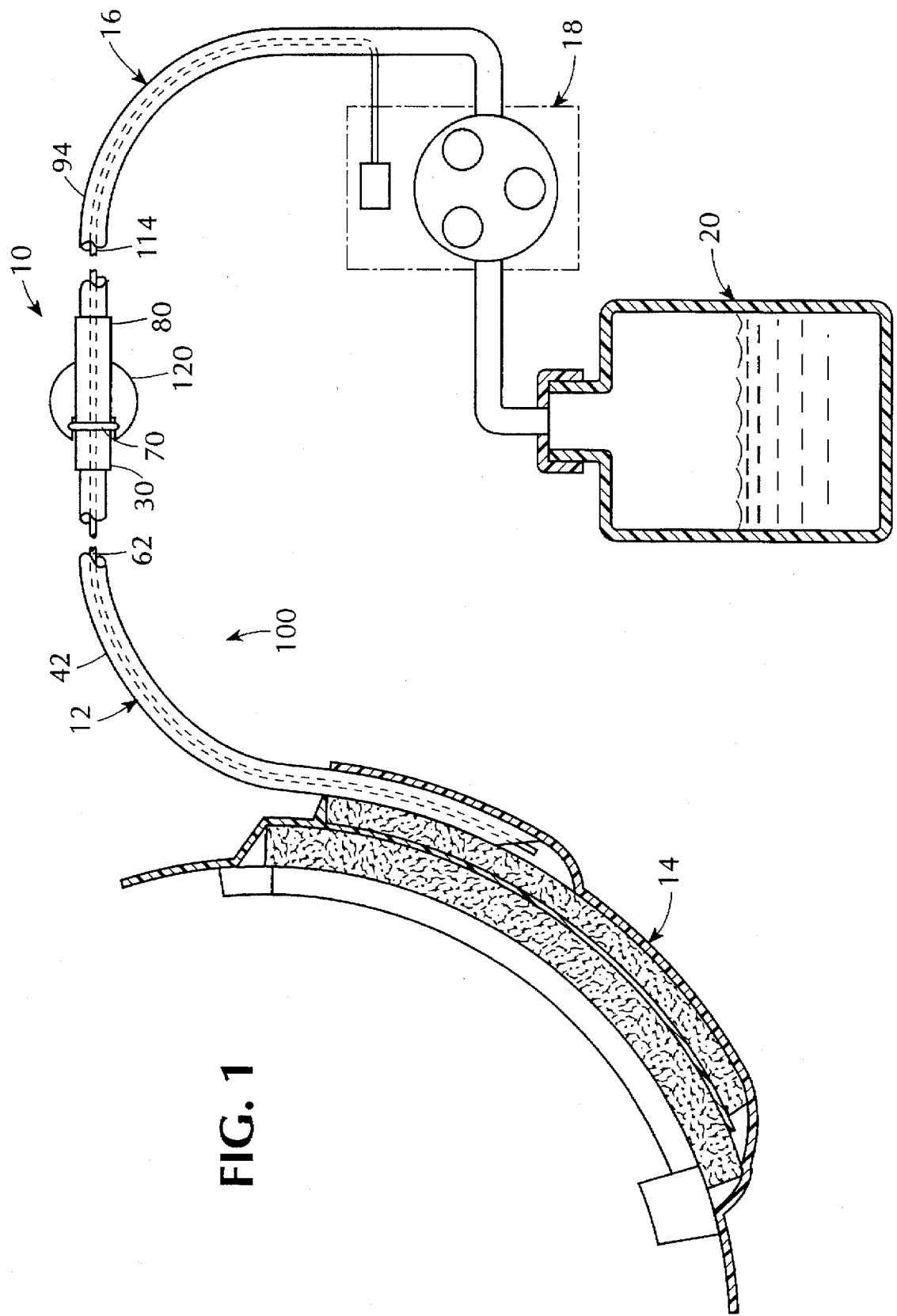
FIG. 1 is a simplified schematic view of a drainage system employing a connector assembly for double tubing that incorporate one embodiment of the invention.

Referring to FIG. 1 of the drawings, a female incontinence drainage system 100 employs a connector assembly 10 for double tubing that incorporates one embodiment of the invention. Although the connector assembly 10 is shown in combination with the drainage system 100, other uses of the connector assembly 10 are contemplated and will become apparent to those skilled in the art.

The drainage system 100 includes a double tube section 12 and a female incontinence device 14 connected to one side of the connector assembly 10. A double tube section 16 with a vacuum pump 18 and a waste collection container 20 are connected to the other side of the connector assembly 10.

Figure 2:
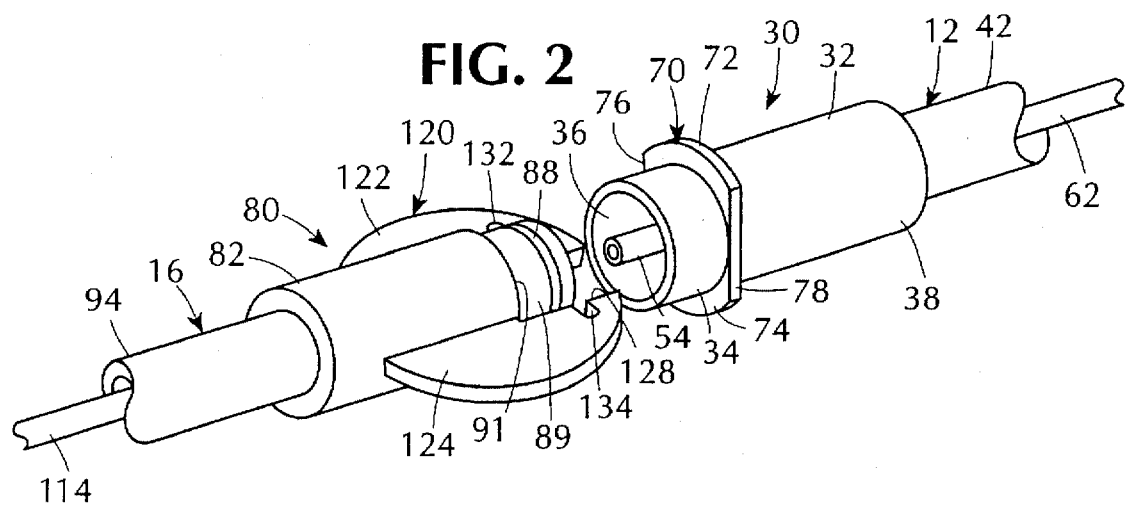
FIG. 2 is a perspective view of the connector assembly double tubing shown in unengaged condition.

Referring to FIGS. 2 and 5, the connector assembly 10 includes a female coupling member 30 engageable with a male coupling member 80.

The female coupling member 30 includes a generally cylindrical outer sleeve 32, preferably formed of a suitable plastic, such as commodity grade, medical polyester, polycarbonate or polyvinyl chloride. If desired, the female coupling member 30 can be molded or otherwise formed as a one-piece component.

An engagement end 34 of the outer sleeve 32 includes a female engagement opening 36. An opposite tube-receiving end 38 of the outer sleeve 32 includes a tube-receiving opening 40 that accommodates an outer tube 42 of the double tube section 12. The outer tube 42 is joined in leak-tight fashion in any suitable known manner to an inner surface 52 of the outer sleeve 32.

A core section 42 (FIGS. 5 and 8) is formed inside the sleeve 32 between the engagement opening 36 and the tuber-receiving opening 40. The core section 42 includes three radial arms 46, 48 and 50 that join the inside surface 52 of the outer sleeve 32. The radial arms 46, 48 and 50 have a common center and intersect to form a central inner sleeve 54. One end 56 of the inner sleeve 54 terminates at the tube-receiving opening 40. An opposite end 58 of the inner sleeve 54 projects beyond the engagement end 34 of the outer sleeve 32.

The inner sleeve 54 defines an inner tube-receiving space 60 (FIG. 5) for concentric accommodation of an inner tube 62 of the double tube section 12. The inner tube 62 is joined in leak-tight fashion in any suitable known manner to the inner sleeve 54.

The radial arms 46, 48 and 50 of the core 42 define fluid passage spaces 62, 64 and 66 (FIG. 8) that provide communication between the engagement opening 36 and the tuber-receiving opening 40. It should be noted that any number of radial arms 46, 48 and 50 can be used as long as an acceptable amount of fluid flow is obtained through the voids or fluid passage spaces 62, 64 and 66 defined by the arms.

The cylindrical sleeve member 32, which is elongated about its cylindrical axis, includes a transverse latch 70. The transverse latch 70 has two flange-like opposite locking sections 72 and 74 that project radially from the exterior surface of the sleeve member 32. The latch 70 also includes two opposite parallel sections 76 and 78 that are tangent to the surface of the sleeve member 32 and define nonlatching portions of the latch 70. The tangent sections 76 and 78 form opposite side edges of the locking sections 72 and 74.

The male coupling member 80 (FIGS. 2 and 5) includes a generally cylindrical outer sleeve 82, also preferably formed of a suitable plastic, such as commodity grade, medical polyester, polycarbonate or polyvinyl chloride. If desired, the male coupling member 80 can be molded or otherwise formed as a one-piece component.

The outer cylindrical sleeve 82 has a male engagement end portion 84 formed with an opening 86. An O-ring 88 is provided at a reduced shoulder 89 of the engagement end portion 84. The reduced shoulder 89 extends to a stop portion 91.

An opposite tube-receiving end 90 of the outer sleeve 82 has a tube-receiving opening 92 that accommodates an outer tube 94 of the double tube section 16. The outer tube 94 is joined in leak-tight fashion in any suitable known manner to the inner surface 108 of the outer sleeve 82.

A core section 96 (FIGS. 5 and 7) similar to the core section 42 is formed inside the sleeve 82 between the end opening 86 and the tube-receiving opening 92. The core section 96 includes three radial arms 102, 104 and 106 (FIG. 7) that join the inner surface 108 of the outer sleeve 82. The arms 102, 104 and 106 have a common center and intersect to form a central inner sleeve 110.

The inner sleeve 110 accommodates a male tube fitting 112 that has an axial bore 113 and is preferably formed of non-corrosive metal, such as brass. The male fitting 112 occupies a portion of the inner sleeve 110 and has a reduced diameter end portion 115 that extends from the core section 96 into the end opening 86. Alternatively, the male fitting 112 can be molded integrally with the inner sleeve 110, which sleeve 110 can be molded integrally with the sleeve 82.

The portion of the inner sleeve 110 that does not occupy the male fitting 112 receives an inner tube 114 of the double tube section 16. The inner tube 114 is joined in leak-tight fashion in any suitable known manner to the inner surface of the inner sleeve 110.

The radial arms 102, 104 and 106 of the core section 96 define fluid passage spaces 116, 117 and 118 (FIG. 7 that provide communication between the end opening 86 and the tube-receiving opening 92.

The sleeve member 82, which is elongated along its cylindrical axis, includes a latch 120 (FIG. 2) having two oppositely disposed wing-like latch sections 122 and 124 that extend longitudinally of the exterior surface of the outer sleeve 82.

Each of the latch sections 122 and 124, which project radially from the exterior surface of the outer sleeve member 82, have respective parallel inside edges 126 and 128 (FIG. 6). The inside edges 126 and 128 are transversely spaced from the reduced shoulder 89 of the end portion 84. Transversely aligned locking recesses or slots 132 and 134 are respectively formed in the inside edges 126 and 128 of the latch sections 122 and 124.

Referring to FIG. 1, the connector assembly 10 is used to connect the two double tube sections 12 and 16 of the drainage system 100. However, the concepts and structure of the connector assembly 10 are applicable to other systems, as will be understood by those skilled in the art.

The connector assembly 10 of the drainage system 100 permits separation of the female incontinence device 14 from the pump 18 and the waste container 20. The incontinence device 14 and the double tubing section 12 with the coupling member 30 can thus be packaged as a separate unit. If the double tubing section 12 and coupling member 30 are to be reused, the incontinence device 14 can be conveniently replaced from the double tubing section 12.

Separability of the pump 18 and the waste container 20 from the incontinence device 14 also permits convenient disposal of the waste container 20 and facilitates servicing, operation or replacement of the vacuum pump 18.

The coupling members 30 and 80 are engaged by aligning the latches 70 and 120 in the manner shown in FIG. 2. Thus, the latch sections 122 and 124 of the coupling member 80 are oriented to register with the nonlatching sections 76 and 78 approximately at their points of tangency to the coupling member 30 when initial engagement of the coupling members 30 and 80 is established.

The reduced shoulder section 89 of the coupling member 80 is receivable in the engagement opening 36 of the coupling member 30 in the manner shown in FIG. 6.

As most clearly shown in FIG. 6, the distance between the inside edges 126 and 128 of the latch 120 is greater than the outside diameter of the outer sleeve 32 of the coupling member 30. Thus, as the engagement end 84 of the coupling member 80 telescopes in the engagement opening 36 of the female coupling member 30, the inside edges 126 and 128 of the latch member 120 clear the tangent portion of the nonlatching sections 76 and 78 of the latch 70.

The coupling members 30 and 80 are fully engaged when the end portion 34 of the female coupling member 30 abuts the stop portion 91 of the male coupling member 80. Such engagement, which provides substantial surface to surface contact, enables the reduced diameter end portion 116 of core section 96 to be received in leak-tight fashion in the sleeve space 60 of the core section 42.

Under this arrangement the fitting 112 of the coupling member 80, which forms a continuation of the inner tube 114, also forms a continuation of the inner tube 62 of the coupling member 30. Thus, fluid can flow without leakage from the inner tube 62 through the fitting 112 and into the inner tube 114.

Engagement of the coupling members 30 and 80 also provides a leak-tight fluid flow path between the outer tube 42 of the coupling member 30 and the outer tube 94 of the coupling member 94.

For example, fluid which flows through the outer tube 42 of the coupling member 30 passes through the fluid passage spaces 62, 64 and 66 of the core 42 into the openings 36 and 86 of the engaged coupling members. Fluid then passes through the fluid passage spaces 116, 117 and 118 of the core 96 and into the outer tube 94 of the coupling member 80.

The O-ring 88 at the shoulder section 89 of the coupling member 80 ensures that the connection between the coupling members 30 and 80 is leak-tight. Alternatively the O-ring 88 can be omitted by sizing the shoulder section 89 of the coupling member 80 and the engagement opening 36 of the coupling member 30 to have a leak-tight frictional or interference engagement.

There is no communication between the fluid line established by the outer tubes 42, 94 and the fluid line established by the inner tubes 62, 114 within the double tube sections 12 and 16.

Figure 3:
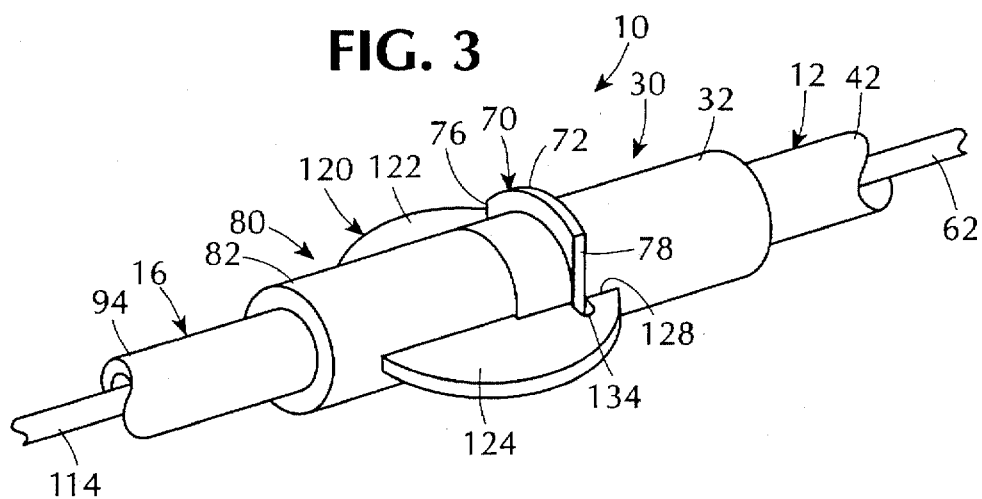
FIG. 3 is a schematic view thereof in engaged but unlocked condition.

With the coupling members 30 and 80 engaged as shown in FIG. 3 there is leak-tight communication between the respective inner tube sections 62, 114 and the respective outer tube sections 42, 94 of the double tube assemblies 12, 16. However, in the engagement position as shown in FIG. 3, the connector assembly 10 is in unlocked engagement, since the tangent portions of the nonlatching sections 76 and 78 are transversely aligned with the latch slots 130 and 132. Thus, the coupling members 30 and 32, although engaged, are separable from each other upon imposition of opposite forces on each coupling member directed away from each other.

Figure 4:
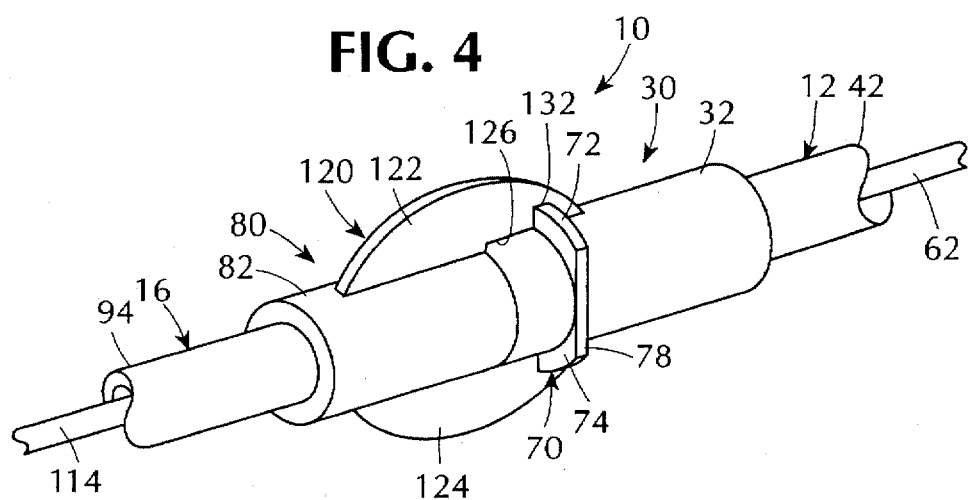
FIG. 4 is a schematic view thereof in a engaged and locked condition.

With the coupling members 30 and 80 in the unlocked engagement of FIG. 3, axial rotation of one of the coupling members 30, 80 with respect to the other coupling member enables the latch sections 72 and 74 to be received in the latch slots 130 and 132 and thereby place the coupling members 30, 80 in locked engagement, as shown in FIG. 4.

Axial rotation of one of the engaged coupling members 30, 80 with respect to the other engaged coupling member does not upset the leak-tight fluid flow relationship between the inner tubes 62, 114 and the outer tubes 42, 94, since the inner and outer tubes axially rotate or twist through the desired rotation angle as a unit with the coupling members. Axial rotation of approximately 60° to 90° will suffice to change the engagement between the coupling members from an unlocked engagement to a locked engagement, and vice-versa. However the system can be designed for a greater or lesser axial rotation to accomplish the desired transition from locked to unlocked engagement of the coupling members based on the angular extent of the latch sections 72 and 74.

The substantial surface to surface contact between the fitting 112 and the inner sleeve 54, and the O-ring seal between the coupling members 30 and 80 maintain a leak-tight seal during any axial rotation of one coupling member relative to the other.

Frictional contact between the engaging surfaces of the coupling member 30 and the coupling member 80 maintain the latches 70 and 120 in any desired orientation, such as the locked condition of FIG. 4.

When separation of the coupling members 30 and 80 is desired, one of the coupling members 30, 80 is rotated with respect to the other coupling member to align the latch slots 130 and 132 of the coupling member 80 with the approximate point of tangency of nonlatching tangent sections 76 and 78 of the coupling member 30. Oppositely directed forces on each of the coupling members 30 and 80 will serve to disengage and separate the coupling members, as shown in FIG. 2.

Thus, repeated engagement locking, unlocking and disengagement of the respective coupling members 30 and 80 is quickly and easily accomplished.

Another embodiment of the connector assembly is generally indicated by the reference number 150 in FIG. 9. The connector assembly 150 includes a female coupling member 160 and a male coupling member 170. The female coupling member 160 is of generally cylindrical shape, and is similar to the outer sleeve member 32 of the coupling member 30, minus the core section 42.

The female coupling member 160 has an engagement opening 162 at one end, and a tube receiving opening 164 at the opposite end for receiving a tube 166. A reduced diameter section 168 is provided between the openings 162 and 164. The exterior surface of the coupling member 160 is provided with the latch 70.

The male coupling member 170 is also of generally cylindrical shape, with an inside tube-receiving surface 172 for receiving a tube 174. An engagement end 176 of the coupling 170 has a reduced diameter shoulder portion 178 that is provided with an O-ring 180. The reduced diameter shoulder 178 terminates in a stop portion 182. The coupling member 170 also includes the latch 120.

The coupling members 160 and 170 are initially engaged in an unlocked condition corresponding to FIG. 3 in a manner similar to that previously described for the coupling members 30 and 80. Once the coupling members 160 and 170 are in unlocked engagement, a condition of locked engagement corresponding to FIG. 4 is established by axially rotating one of the coupling members 160, 170 approximately 60° to 90° with respect to the other coupling member. The coupling members 160 and 170 can also be designed to rotate a lesser or greater amount than 60° to 90° to accomplish the desired transition from locked to unlocked engagement based on the angular extent of the latch sections 72 and 74.

Separation of the engaged coupling members 160 and 170 is accomplished by axially rotating one of the coupling members 160, 170 relative to the other coupling member to a position of unlocked engagement corresponding to FIG. 3. Oppositely directed forces on each of the coupling members in unlocked engagement will serve to pull the engaged coupling members away from each other for separation.

As described with respect to the connector assembly 10, the connector assembly 150 can be repeatedly engaged, disengaged, locked and unlocked without affecting the integrity of the leak-tight seal provided between the coupling members 160, 170 and the respective tubes 166 and 174 connected to the coupling members.

Some advantages of the present invention evident from the foregoing description include a connector assembly for double tubing that does not interfere with the flow passages of the respective inner tubes and is easily operable to place the respective coupling members in a locked condition or an unlocked condition. Engagement of the coupling members and separation of the engaged coupling members from their engaged position is easily accomplished.

Upon axially rotating one of the engaged coupling members a predetermined amount relative to the other engaged coupling member, positions of locked or unlocked engagement are obtained. Unlocked engagement leads to easy separation of the coupling members by pulling them apart in opposite directions. Since the connector assembly has no moving parts, it is essentially maintenance free and requires no special skills for use in the manner described. Each coupling member is manufacturable as a one-piece element. For example, the inner fitting 12 of the male coupling member 80 can be molded as an integral part of the core section 96 and the O-ring 88 of the coupling member 80 can be eliminated by providing a frictional leak tight engagement of the coupling members at the shoulder 89 and the engagement opening 36. The female coupling member 30 can be formed as a one piece element as previously described.

The latches of each coupling member are adaptable to connector assemblies for single tubing as well as double tubing. If desired, multiple inner tubes can be provided in the connector assembly without affecting fluid flow, since the latch structure is on an external surface of the coupling members and does not interfere with fluid flow. As the coupling members are suitable for one-piece manufacture, they can be employed in disposable tubing systems.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A connector assembly comprising, a) a pair of separable coupling members, each coupling member having first and second fluid passageways, said coupling members being mutually engageable in a leak-tight fluid flow position wherein said first passageway of each coupling member and said second passageway of each coupling member are in respective, leak-tight fluid communication, b) latch means on each of said coupling members for releasably locking said coupling members together in said fluid flow position, c) said latch means of each of said coupling member being positionable in a first nonlatching position corresponding to unlocked engagement of said coupling members in said fluid flow position, said coupling members in said unlocked engagement being separable upon imposition of opposite forces on each said coupling member, directed away from each other, and d) one of said coupling members being rotatable with respect to the other said coupling member when said coupling members are engaged in said fluid flow position to position said latch means of said one coupling member in a second latched position with respect to the latch means of said other coupling member, said coupling members in said second latched position being in locked engagement in said fluid flow position such that said coupling members cannot be separated upon imposition of said oppositely directed forces on each said coupling member.

2. The connector assembly as claimed in claim 1, wherein said coupling members have generally cylindrical engaging portions to permit axial rotation of said one coupling member with respect to said other coupling member in said fluid flow position, to accomplish movement of said latch means of said one coupling member from said first unlatched position to said second latched position relative to said latch means of said other coupling member.

3. The connector assembly as claimed in claim 1, wherein said latch means are provided on an exterior surface of each of said coupling members.

4. The connector assembly as claimed in claim 1, wherein the latch means of said one coupling member has a first latching section and the latch means of said other coupling member has a second latching section and a nonlatching section, said coupling members being positionable such that said nonlatching section is aligned with the first latching section to permit engagement and disengagement of said coupling members in said fluid flow position.

5. The connector assembly as claimed in claim 4, wherein said first latching section includes a receiving portion to receive said second latching section, axial rotation of said one coupling member with respect to said other coupling member in said fluid flow position providing movement of the receiving portion of the first latching section into alignment with the second latching section to lock said coupling members together in said fluid flow position.

6. The connector assembly as claimed in claim 1, wherein said coupling members are elongated along a longitudinal axis, said latch means of said one coupling member including a first latch flange, said first latch flange having a latch-receiving recess, said latch means of said other coupling member including a second latch flange, said second latch flange being engageable within the latch-receiving recess of said first latch flange upon axial rotation of said one coupling member relative to said other coupling member to lock said coupling members in said fluid flow position.

7. The connector assembly as claimed in claim 6, wherein the latch means of said other coupling member include a nonlatching section at said second latch flange, said nonlatching section being alignable with said first latch flange to permit unlocked engagement of said coupling members in said fluid flow position.

8. The connector assembly as claimed in claim 7, wherein the latch-receiving recess in said first latch flange and said second latch flange are positioned on said respective coupling members such that in said fluid flow position axial rotation of said one coupling member 60° to 90° with respect to said other coupling member moves said coupling members from said unlocked engagement to said locked engagement.

9. The connector assembly as claimed in claim 1, wherein said coupling members have a longitudinal axis and are axially rotatable with respect to each other when said coupling members are engaged together in said fluid flow position, to transversely rotate the latch means of each said coupling member from the first nonlatching position to the second latched position.

10. The connector assembly as claimed in claim 1, wherein each of said coupling members is tubular and includes a sleeve portion for holding an outer tube and a core section for holding an inner tube within the confines of the outer tube.

11. The connector assembly as claimed in claim 10, wherein the core section of one of said coupling members includes a male extension portion and the core section of said other coupling member includes a female extension portion, said male and female extension portions being engageable in leak-tight relationship when said first and second coupling members are engaged in said fluid flow position.

12. The connector assembly as claimed in claim 10, wherein said coupling members each include opposite ends with openings formed therein and each of said core sections is disposed between the opposite end openings of the respective coupling members, said core sections including fluid passages to permit communication between the opposite end openings of the respective coupling members.

13. The connector assembly as claimed in claim 10, wherein said latch means are provided on an exterior surface of each of said sleeve portions to avoid interference of said latch means with the inner tubes held by the respective core sections.

14. A connector assembly comprising a pair of engageable tubular coupling members, engageable latch components on each of said coupling members, said coupling members being axially rotatable in an engaged fluid flow condition from an unlatched position wherein said coupling members are separable, to a latched position, wherein said coupling members are inseparable.

15. The connector assembly as claimed in claim 14, wherein the latch components of one of said coupling members includes an axially extending flange with a slot and the latch component of the other said coupling member includes a transverse flange engageable in the slot of the first latch component upon rotation of one of the engaged coupling members relative to the other said engaged coupling member, such that engagement of the transverse flange in the slot locks the coupling members in the fluid flow position.

16. A method of releasably connecting a pair of engageable coupling members comprising, a) providing two engageable coupling member, each of said coupling member having first and second fluid passageways, b) forming a first latch component on one coupling member to extend transversely of the one coupling member, c) forming a second latch component on the other coupling member to extend longitudinally of the other coupling member, d) locating the latch components on the respective coupling members such that the latch components are transversely aligned when the coupling members are engaged, e) providing a nonlatching section at one of the latch components to permit passage of the other latch component across the nonlatching section when the coupling members are engaged such that the coupling members are in unlocked engagement, and said first passageway of each coupling member and said second passageway of each coupling member are in respective, leak-tight fluid communication, f) providing a recess in one of the latch components to receive the other latch component when one of the engaged coupling members is axially rotated a predetermined amount with reset to the other engage coupling member, said first and second fluid passageways remaining in respective, leak-tight fluid communication, and g) axially rotating one of the engage coupling members the predetermined amount with respect to the other engage coupling member to enable the recess in the one said latch component to engage the other said latch component to lock the engaged coupling members together with said first and second fluid passageways remaining in respective, leak-tight communication.

17. The method of claim 16, including providing supports for double tubing on each of the coupling members to support an inner tube within the confines of an outer tube.

18. The method of claim 16, including locating the first and second latch components on the outside of the coupling members.

19. The method of claim 16, maintaining one of the engaged coupling members freely axially rotatable with respect to the other engaged coupling member into and out of locking engagement.

20. The method of claim 16, maintaining one of the engaged coupling members axially rotatable with respect to the other engaged coupling member in a clockwise or counterclockwise direction to place the engaged coupling members in locked or unlocked engagement, depending upon the rotational engagement and disengagement of the latch components.

21. The connector assembly as claimed in claim 1 wherein one coupling member has a projection portion extending from said first fluid passageway and said other coupling member has a mating receptacle potion for receiving said projection portion in a fluid-tight manner when in said fluid flow position.

22. The connector assembly as claimed in claim 21, wherein said coupling members are cylindrically and one coupling member is a male connector and the other coupling member is a female connector.

23. The method of claim 16, including providing one coupling member with a projection portion extending from said first fluid passageway, and providing said other coupling member with a mating receptacle portion for receiving said projection portion in a leak-tight manner.

* * * * *